United States Patent [19]
Weller, III

[11] Patent Number: 5,378,704

[45] Date of Patent: Jan. 3, 1995

[54] NON-PEPTIDIC ANGIOTENSIN-II-RECEPTOR-ANTAGONISTS

[75] Inventor: Harold N. Weller, III, Pennington, N.J.

[73] Assignee: E.R. Squibb & Sons, Inc., Princeton, N.J.

[21] Appl. No.: 870,007

[22] Filed: Apr. 15, 1992

[51] Int. Cl.$^6$ .... C07D 285/24; C07D 417/04/417/14; A61K 31/54

[52] U.S. Cl. .................................. 514/222.8; 514/80; 514/81; 514/223.2; 544/10; 544/12

[58] Field of Search ............... 544/12, 10; 514/222.8, 514/223.2, 80, 81

[56] References Cited

U.S. PATENT DOCUMENTS 4,870,186  9/1989  Aldrich ........................ 548/215

FOREIGN PATENT DOCUMENTS 2027839  4/1991  Canada .
2033121  6/1991  Canada .
253310   1/1988  European Pat. Off. .
412848   2/1990  European Pat. Off. .
411766   2/1991  European Pat. Off. .

OTHER PUBLICATIONS

J. H. Freeman et al., "1,2,4–Benzothiadiazine Dioxides and 3,4–Dihydro-3,4–Dihydro-1,2,4–Benzothiadiazine Dioxides", J. Org. Chem 16, 815 (1951).

Chemical Abstract, 58, 4570f (1963).

K. S. Atwal et al., "Substituted 1,4-Dihydropyrimidines. 3. Synthesis of Selectively Functionalized 2-Hetero-1,4-dihydropyrimidines", J. Org. Chem 54, 25 (1989), pp. 5898–5907.

*Primary Examiner*—John M. Ford
*Attorney, Agent, or Firm*—Ellen K. Park

[57] ABSTRACT

Novel compounds having the formula

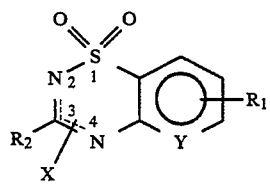

I wherein $R_1$, $R_2$, X and Y are as defined herein. These compounds inhibit the action of angiotensin II and are useful, therefore, for example, as antihypertensive agents.

19 Claims, No Drawings

NON-PEPTIDIC ANGIOTENSIN-II-RECEPTOR-ANTAGONISTS

Field of the Invention

The present invention relates to novel substituted biphenyl derivatives useful as antihypertensive agents.

Summary of the Invention

In accordance with the present invention, novel compounds which inhibit the action of the hormone angiotensin II are disclosed. These compounds are of the general formula

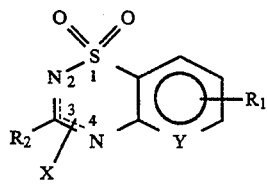

and pharmaceutically acceptable salts and prodrugs thereof.

As used in formula I, and throughout the specification, the symbols have the following meanings:

the broken lines between the nitrogen atoms represent the presence of double bonds, wherein either the 2,3-position is bonded by a double bond and the 4-position nitrogen atom bears the group X, or the 3,4-position is bonded by a double bond and the 2-position nitrogen atom bears the group X, where the group X is

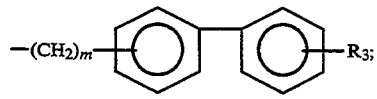

Y is a carbon or nitrogen atom;
$R^1$ is hydrogen, $-CO_2R_4$, $-COR^4$, perfluoroalkyl, halogen, cyano or

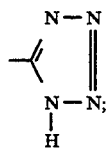

$R_2$ is hydrogen, alkyl, alkenyl, alkynyl, arylalkyl, $-OR_7$ or $-SR_7$ bonded to the ring system by a single bond or $R_2$ is O or S bonded to the ring system by a double bond to form a carbonyl or thiocarbonyl group;
$R_3$ is

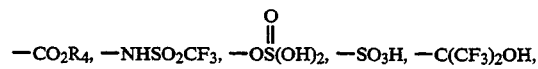

-continued

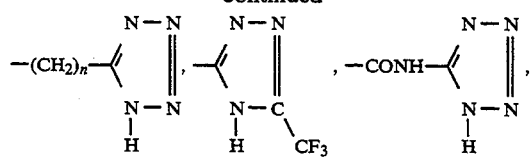

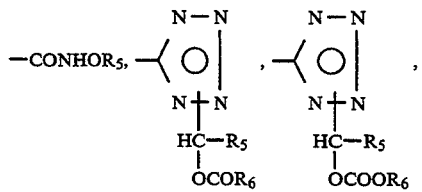

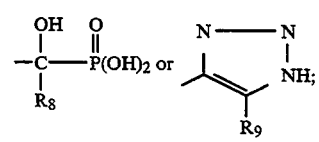

$R_4$ is hydrogen, alkyl, perfluoroalkyl of 1 to 8 carbon atoms, cycloalkyl of 3 to 6 carbon atoms, phenyl benzyl

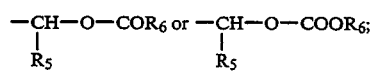

$R_5$ is hydrogen, alkyl, aryl, arylalkyl or cycloalkyl;
$R_6$ is alkyl, aryl, alkylaryl, arylalkyl or cycloalkyl;
$R_7$ is hydrogen, alkyl, alkenyl, alkynyl, aryl or arylalkyl;
$R_8$ is hydrogen, alkyl of 1 to 5 carbon atoms or phenyl;
$R_9$ is $-CN$, $-NO_2$ or $-CO_2R_4$,
m is an integer of 1 to 5; and
n is 0 or the integer 1.

Detailed Description of the Invention

The present invention relates to the compounds of formula I (and pharmaceutically acceptable salts and prodrugs thereof), to pharmaceutical compositions employing such compounds and to methods of using such compounds. Listed below are definitions of various terms used to describe the compounds of the instant invention. These definitions apply to the terms as they are used throughout the specification (unless they are otherwise limited in specific instances) either individually or as part of a larger group.

The term "alkyl" refers to both straight and branched chain groups having 1 to 10 carbon atoms. Alkyl groups having 1 to 4 carbon atoms are preferred.

The terms "alkenyl" and "alkynyl" refer to both straight and branched chain groups. Those groups having 2 to 10 carbon atoms are preferred.

The term "cycloalkyl" refers to groups having 3 to 8 carbon atoms.

The term "alkoxy" refers to groups having 1 to 8 carbon atoms. Alkoxy groups having 1 to 3 carbon atoms are preferred.

The term "halogen" refers to fluorine, chlorine, bromine and iodine with fluorine and chlorine being preferred.

The term "aryl" refers to phenyl or naphthyl or phenyl or naphthyl substituted with substituents selected from halogen, alkyl, alkoxy, carboxy, alkylthio, hydroxy, alkanoyl, nitro, amino, alkylamino, dialkylamino or trifluoromethyl groups. Preferred aryl groups are phenyl and monosubstituted phenyl and phenyl is most preferred.

The term "salt(s)" refers to acidic and/or basic salts formed with inorganic and organic acids and bases. The nontoxic, pharmaceutically acceptable salts are preferred, although other salts are also useful, for example, in isolation or purification steps which may be employed during preparation.

It should be understood that the present invention includes prodrug forms, such as ester, acetal and/or mixed acetal derivatives of the compounds of formula I. For example, such derivatives have been documented in *Design of Prodrugs*, edited by H. Bundgard, (Elsevier, 1985) and *Methods in Enzymology*, Vol. 42, p. 309-396, edited by K. Widder et al. (Academic Press, 1985). Further, it is understood that any moiety at $R_3$ that will be cleaved in vivo to provide an acidic $R_3$ moiety is within the spirit and scope of this invention.

An exemplary process for preparing the compounds of formula I includes coupling a compound of formula II

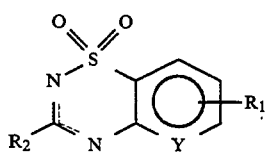

with a compound of formula III

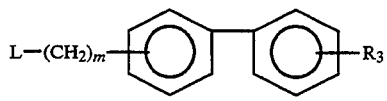

where L is a leaving group such as a halogen, using a base such as potassium carbonate in an organic solvent such as dimethylformamide.

Compounds of formula II where $R_2$ is —$SR_7$ or —$OR_7$ and $R_7$ is hydrogen, are prepared by condensation of an aminosulfonamide of formula IV

with a compound of formula V

where $R_2$ is sulfur or oxygen and Z is selected from chloro, amino, imidazole, —O—alkyl or —O—aryl, such as phosgene or thiophosgene or an equivalent reagent such as (thio)carbonyldiimidazole, (thio)urea, dialkyl or diaryl (thio)carbonate, etc. in an inert solvent such as dimethylformamide or dichloromethane to give compounds of formula VI

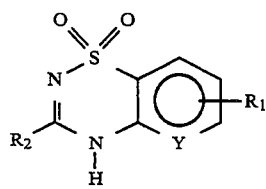

Compounds of formula VI where $R_2$ is sulfur may also be prepared by methods disclosed in *Chemical Abstracts*, 58, 4570f (1963).

Compounds of formula II where $R_2$ is alkylthio or alkoxy can be prepared from compounds of the formula II where $R_2$ is —SH or —OH by treatment with an alkylating agent of the formula $R_7$—L (where $R_7$ and L are as previously defined), such as 1-iodopropane and a base such as potassium carbonate in an organic solvent such as dimethylformamide.

Compounds of formula II where $R_2$ is hydrogen, alkyl, alkenyl, alkynyl, or arylalkyl, can be prepared by methods disclosed in *J. Org. Chem.*, 16, 815 (1951) and references cited therein, such as by reaction of compounds of formula IV with an alkyl orthoester such as alkyl-$C(OCH_3)_3$ to give compounds of formula II, which may then be coupled to compounds of formula III as described previously.

Compounds of formula III can be prepared by methods disclosed in European Patent Application No. 0253310, to E. I. DuPont de Nemours and Co., published Jan. 20, 1988; and U.S. Pat. No. 4,870,186 issued Sep. 26, 1986 to Aldrich et al.

Compounds of formula I may also be prepared by reacting compounds of formula III with a compound of formula IV to form compounds of formula VII

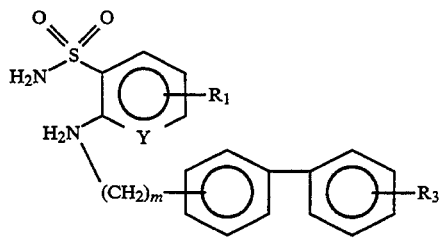

which are then condensed with a compound of formula V to form the formula I compounds.

Preferred compounds of the present invention are those wherein:

$R_1$ is —$CO_2H$;

$R_2$ is —$OR_7$ or —$SR_7$, where $R_7$ is alkyl;

$R_3$ is —$CO_2H$ or tetrazolyl and is bonded at the 2-position;

Y is carbon; and m is the integer 1.

All stereoisomers of the compounds of the instant invention are contemplated, either in admixture or in pure or substantially pure form.

The present compounds of formula I inhibit the action of the hormone angiotensin II (A-II) and are therefore useful, for example, as antihypertensive agents.

The action of the enzyme renin on angiotensinogen, a pseudoglobulin in blood plasma, produces angiotensin I. Angiotensin I is converted by angiotensin converting enzyme (ACE) to A-II. The latter is an active pressor substance which has been implicated as the causative agent in several forms of hypertension in various mammalian species, e.g., humans.

The compounds of this invention inhibit the action of A-II at its receptors on target cells and thus prevent the increase in blood pressure produced by this hormone-receptor interaction. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 0.1 to 100 mg per kilogram of body weight per day, preferably about 1 to 15 mg per kilogram of body weight per day is appropriate to reduce blood pressure.

The composition is preferably administered orally, but intranasal, transdermal and parenteral routes such as the subcutaneous, intramuscular, intravenous or intraperitoneal routes can also be employed. Further the compounds of this invention are believed to be useful in the treatment of congestive heart failure and cardiac hypertrophy. In addition, in view of the role of these compounds in the renin-angiotensin system described above, the A-II antagonist compounds disclosed herein are also expected to be useful for the same or similar indications which have developed for ACE inhibitors.

The compounds of this invention can also be formulated in combination with a diuretic for the treatment of hypertension. A combination product comprising a compound of this invention and a diuretic can be administered in an effective amount which comprises a total daily dosage of about 30 to 600 mg, preferably about 30 to 330 mg of a compound of this invention, and about 15 to 300 mg, preferably about 15 to 200 mg of the diuretic, to a mammalian species in need thereof. Exemplary of the diuretics contemplated for use in combination with a compound of this invention are the thiazide diuretics, e.g., chlorthiazide, hydrochlorthiazide, flumethiazide, hydroflumethiazide, bendroflumethiazide, methylchlothiazide, trichlormethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration, in sterile solutions or suspensions for parenteral or intranasal administration, or in transdermal patches. About 10 to 500 mg of a compound of formula I is compounded with a physiologically acceptable vehicle, carrier, excipient, binder, preservative, stabilizer, flavor, etc., in a unit dosage form as called for by accepted pharmaceutical practice. The amount of active substance in these compositions or preparations in such that a suitable dosage in the range indicated is obtained.

The following examples and preparations describe the manner and process of making and using the invention and are illustrative rather than limiting. It should be understood that there may be other embodiments which fall within the spirit and scope of the invention as defined by the claims appended hereto.

EXAMPLE 1

4'-[(3-Butyl-2H-1,2,4-benzothiadiazin-2-yl)methyl][1,1'-biphenyl]-2-carboxylic acid, 1,1-dioxide A. 3-Butyl-2H-1,2,4-benzothiadiazine, 1,1-dioxide A solution of 2-aminobenzenesulfonamide (1.72 g, 10 mmol) and trimethylorthovalerate (5.2 mL, 30 mmol) was heated to 130° C. for three hours and then allowed to cool to room temperature. A precipitate formed and was isolated by filtration, washed with toluene, and dried in vacuo to yield the title compound as colorless crystals (1.85 g, 7.8 mmol, 78%); m.p. 153°–155° C.

B. 4'-(Bromomethyl)[1,1'-biphenyl]-2-carboxylic acid, 1,1-dimethylethyl ester 1. 4'-Methyl[1,1'-biphenyl]-2-carboxylic acid, 1,1-dimethylethyl ester (Reference: European Patent Application 87-109919.8 Example 85a, page 148, line 22)

To a solution of 4'-methyl-[1,1'-biphenyl]-2-carboxylic acid (25.0 g, 0.118 mol) in dichloromethane (120 mL) at 0° C. was added oxalyl chloride (2.0M solution in methylene chloride, 470 mL, 0.940 mol) over 30 minutes. The solution was warmed to 25° C., stirred for three hours and concentrated in vacuo to remove excess oxalyl chloride. The remaining residue was suspended in diethyl ether (300 mL), cooled to 0° C. and potassium t-butoxide (26.44 g, 0,236 mol) was added over 15 minutes keeping the temperature of the mixture between 15°–25° C. The mixture was allowed to warm to 25° C. and was stirred for one hour, poured into water (200 mL), and extracted with diethyl ether. The ether extract was then washed with aqueous sodium bicarbonate (saturated solution), dried (magnesium sulfate) and concentrated in vacuo to an amber oil. Subsequent distillation (124°–130° C., 0.6 mm Hg) yielded the title compound as a colorless liquid (27.7 g, 92%).

2. 4'-(Bromomethyl)[1,1'-biphenyl]-2-carboxylic acid, 1,1-dimethylethyl ester

A mixture of the title A compound (13.42 g, 50.0 mmol), N-bromosuccinimide (8.9 g, 50 mmol) and azo-bisisobutyronitrile (10 mg) was refluxed under argon in carbon tetrachloride (50 mL) for two hours. The mixture was cooled to 25° C. and concentrated in vacuo. The residue was stirred in dichloromethane (200 mL) and filtered to remove insoluble material. The filtrate was then filtered through silica gel (200 g held in a fritted buchner funnel), washed with dichloromethane (200 mL), and concentrated to dryness in vacuo. Recrystallization of the solid residue from petroleum ether (16.55 g in 800 mL) produced the title compound, as a white crystalline solid (14.0 g, 72% yield, purity by HPLC =92%); m.p. 98°–101° C.

C. 4'-[(3-Butyl-2H-1,2,4-benzothiadiazin-2-yl)-methyl][1,1'-biphenyl]-2-carboxylic acid, 1,1-dimethylethyl ester, 1,1-dioxide A mixture of the title A compound (1.341 g, 5.3 mmol), the title B compound (2.96 g, 5.3 mmol), and potassium carbonate (777 mg, 5.63 mmol) in dimethylformamide (28 mL) was stirred under argon at 55° C. for 48 hours. The mixture was allowed to cool to room temperature, poured into water (200 mL), extracted with ethyl acetate (3×100 mL), dried (magnesium sulfate), and concentrated in vacuo to yield an amber oil. The crude material was purified using flash chromatography (silica gel eluted with 10:1 and then 3:1 toluene:ethyl acetate and a second silica gel column eluted with chloroform).

Fractions containing the major product were combined to provide the title compound (350 mg, 0.7 mmol, 12%).

D.
4'-[(3-Butyl-2H-1,2,4-benzothiadiazin-2-yl)methyl][1,1'-biphenyl]-2-carboxylic acid, 1,1-dioxide The title C compound (330 mg, 0.65 mmol) was dissolved in a solution of hydrogen chloride in ethyl acetate (35 mL) and stirred at room temperature for two hours. The solvent was removed in vacuo and the resultant oil was dissolved in methanol (15 mL) and water (5 mL) and adjusted to pH 8 with an aqueous solution of lithium carbonate (0.1M). This solution was concentrated in vacuo to 10 mL and immediately purified using preparative HPLC (polystyrene column, 30 mm×250 mm Jordi Gel, eluting with a gradient from water to methanol). Fractions containing the major component were combined and concentrated and then partially dissolved in ethanol (10 mL) and water (35 mL) and lyophilized to give the title compound as a white solid (120 mg, 0.26 mmol, 40%); m.p. 125°–130° C.

Elemental Analysis (%)

Calc'd: C 64.29; H 5.27; N 6.00; S 6.86; Found: C 64.21; H 5.41; N 6.28: S 6.95.

EXAMPLE 2
4'-[[3-(Propylthio)-2H-1,2,4-benzothiadiazin-2-yl]methyl][1,1'-biphenyl]-2-carboxylic acid, 1,1-dioxide, monolithium salt

A. 2H-1,2,4-benzothiadiazine-3-thiol, 1-dioxide

Using the procedures described in Chem. Abs., 58, 4570f (1963); a mixture of 2-aminobenzene-sulfonamide (6.0 g, 35 mmol) and thiourea (9.0 g, 120 mmol) was heated to 180° C. and stirred at that temperature for two hours, after which it was poured into ice water. The resulting mixture was made basic by addition of sodium bicarbonate, then was filtered. The filtrate was adjusted to pH 3 by addition of concentrated hydrochloric acid and was extracted with ethyl acetate (3×). The extract was dried (magnesium sulfate) and concentrated, and the residue was triturated with ether to give the title compound as a tan solid (3.3 g, 44%); m.p. 198°–199° C.

B. 3-(Propylthio)-2H-1,2,4-benzothiadiazine, 1,1-dioxide

A mixture of the title A compound (420 mg, 2.0 mmol), 1-iodopropane (0.2 ml, 2.0 mmol), and potassium carbonate (276 mg, 4.0 mmol) in dimethylformamide (5 mL) was stirred at 25° C. for one hour, after which it was poured into brine and extracted with ethyl acetate. The extract was dried (magnesium sulfate) and concentrated. The residue was purified by flash chromatography on silica gel (65 g, eluting with 2:1 hexane:ethyl acetate). Fractions containing the major product were combined and concentrated; the residue was triturated with ether to give the title compound as a white solid (265 mg, 52%); m.p. 168°–170° C.

C.
4'-[[3-(Propylthio)-2H-1,2,4-benzothiadiazin-2-yl]methyl][1,1'-biphenyl]-2-carboxylic acid, 1,1-dimethylethyl ester, 1,1-dioxide and
4'-[[3-(Propylthio)-4H-1,2,4-benzothiadiazin-4-yl]methyl][1,1'-biphenyl]-2-carboxylic acid, 1,1-dimethylethyl ester, 1,1-dioxide A mixture of the title B compound (230 mg, 0.90 mmol), the title B compound from Example 1 (520 mg, 1.5 mmol), and cesium carbonate (650 mg, 2.0 mmol) in dimethylformamide (2.5 mL) was stirred for 24 hours at 25° C. Additional title B compound of Example 1 was added (200 mg) and the mixture was stirred at 75° C. for six more hours, after which it was poured into brine and extracted with ethyl acetate. The extract was dried (magnesium sulfate) and concentrated and the residue was purified by flash chromatography on silica gel (300 g), eluting with 4:1 hexane:ethyl acetate to give the title compound as a high $R_f$ isomer (105 mg, 22%) and a low $R_f$ isomer (150 mg, 32%).

D.
4'-[[3-(Propylthio)-2H-1,2,4-benzothiadiazine-2-yl]methyl][1,1'-biphenyl]-2-carboxylic acid, 1,1-dioxide, monolithium salt A solution of the high $R_f$ isomer of the title C compound (85 mg, 0.16 mmol) in acetic acid, saturated with hydrogen chloride (5 mL) was stirred at 25° C. for one hour, after which it was concentrated in vacuo. The residue was dissolved in excess 0.1 N lithium carbonate solution and purified by preparative HPLC (Jordi-Gel polystyrene column, 20×500 mm, eluting with one liter of water then 30 mL/min of a linear gradient from water to methanol over 20 minutes). Fractions having UV absorbance at 254 nm were analyzed by analytical HPLC and those containing the major product were combined and concentrated; the residue was dissolved in ethanol, diluted with water until cloudy, frozen, and lyophilized to give the title compound as a white solid (45 mg, 60%); m.p. 100°–120° C.

Elemental Analysis (%)

Calc'd: C 59.52; H 4.64; N 5.78; S 13.24; Found: C 59.52; H 4.57; N 5.48; S 13.34.

EXAMPLE 3
4'-[(3-Butyl-4H-1,2,4-benzothiadiazin-4-yl)methyl]-[1,1'-biphenyl]-2-carboxylic acid, 1,1-dioxide

A.
4'-[[3-Butyl-4H-1,2,4-benzothiadiazin-4-yl]methyl][1,1'-biphenyl]-2-carboxylic acid, 1,1-dimethylethyl ester, 1,1-dioxide A mixture of the title A compound of Example 1(288 mmol), and the title B compound of Example 1 (400 mg, 1 mmol) and sodium hydride (40 mg, 40% in mineral oil, 1 mmol) in dimethylformamide (5 mL) was stirred under argon at room temperature for 18 hours and then stirred an additional six hours at 55° C. The mixture was allowed to cool to room temperature, poured into brine (100 mL), extracted with ethyl acetate (3×100 mL), dried (magnesium sulfate), and concentrated in vacuo to yield an amber oil. The crude material was purified using flash chromatography (275 g silica eluting with 10:1 and then 3:1 toluene: ethyl acetate). Fractions containing two major unresolvable products, as well as some impurities, were combined and further purified by recrystallization from methanol to provide the title compound (100 mg, 0.2 mmol, 10%).

B. 4'-[(3-Butyl-4H-1,2,4-benzothiadiazin-4-yl) methyl][1,1'-biphenyl]-2-carboxylic acid, 1,1-dioxide The title A compound (100 mg, 0.2 mmol) was dissolved in trifluoroacetic acid (50 mL) and stirred for three hours. Subsequent removal of the solvent in vacuo, trituration of the remaining solid with methanol, and isolation by filtration provided the title compound as a white solid (58 mg, 0.13 mmol; 65%); m.p. 215°–217° C.

Elemental Analysis (%)

Calc'd: C 64.05; H 5.44; N 5.93; S 6.78; F 1.21; Found: C 64.15; H 5.31; N 5.63; S 6.88; F 1.07.

EXAMPLE 4

4'-[[3-(Propylthio)-4H-1,2,4-benzothiadiazin-4-yl]methyl][1,1'-biphenyl]-2-carboxylic acid, 1,1-dioxide A solution of the low $R_f$ isomer of the title C compound of Example 2 (135 mg, 0.26 mmol) in trifluoroacetic acid (5 mL) was stirred at 25° C. for one hour, after which it was concentrated in vacuo. The residue was purified by preparative HPLC (YMC S-10 ODS column, 30×500 mm, eluting with 40 mL/min of 74% aqueous methanol containing 0.1% trifluoroacetic acid). Fractions containing the major product were combined and concentrated; the residue was dissolved in ethanol, diluted with water until cloudy, frozen, and lyophilized to give the title compound as a white solid (95 mg, 77%); m.p. 75°–85° C.

Elemental Analysis (%)

Calc'd: C 58.95; H 4.94; N 5.70; S 13.05; F 0.70; Found: C 58.97; H 4.62; N 5.64; F 13.10; F 0.73.

EXAMPLE 5

4'-[(5,6,7,8-Tetrafluoro-3-methyl-4H-1,2,4-benzothiadiazin-4-yl)methyl][1,1,'-biphenyl]-2-carboxylic acid, 1,1-dioxide

A.
5,6,7,8-Tetrafluoro-3-methyl-2H-1,2,4-benzothiadiazine, 1,1-dioxide

1. 2-Amino-3,4,5,6-tetrafluorobenzene sulfonic acid 2,3,4,5-Tetrafluoroaniline (16.5 g, 0.1 mol) was added dropwise over 20 minutes with stirring to a mixture of chlorosulfonic acid (14 g, 0.12 mol) in tetrachloroethylene (100 mL) with ice bath cooling. A yellow precipitate formed immediately.. When the addition was complete, the mixture was heated at reflux for three hours, during which a light tan granular solid formed. The solid was collected by filtration, washed with ether, and dried in vacuo to give the title compound (25 g); m.p. 272°–276°.

Microanalysis

Calc'd: N 5.71; S 13.07 Found: N 5.92; S 13.12.

2. 2-Amino-3,4,5,6-tetrafluorobenzene sulfonic acid, sodium salt

A solution of 2-amino-3,4,5,6tetrafluorobenzene sulfonic acid (24 g, 97 mmol) in absolute ethanol (500 mL) was added rapidly to a solution prepared from 2.2 g (97 mmol) of sodium in absolute ethanol (150 mL). A light tan precipitate formed immediately. The mixture was allowed to stand overnight at 25° C., after which the solid was collected by filtration to give the title compound (21 g, 80%); m.p. >300° C.

3. 2-Acetamido-3,4,5,6-tetrafluorobenzene sulfonic acid, sodium salt 2-amino-3,4,5,6-tetrafluorobenzene sulfonic acid, sodium salt (5.34 g, 20 mmol) was suspended in acetic anhydride (50 mL) and acetyl chloride (1.6 g, 20 mmol) was added. The mixture was warmed on a steam bath for one hour during which the mixture became clear then a white precipitate formed. The mixture was then cooled to 25° C. and the solid precipitate was collected to give the title compound (4.8 g, 77%); m.p. >300° C.

4. 2-[(1-chloroethylidine)amino]-3,4,5,6-tetrafluorobenzene sulfonyl chloride A mixture of 2-acetamido-3,4,5,6tetrafluorobenzene sulfonic acid, sodium salt (6.18 g, 20 mmol), phosphorus pentachloride (2.1 g) and phosphorus oxychloride (10 mL) was heated at reflux for six hours, after which it was poured into ice water. The mixture was extracted with ether. The extract was dried (magnesium sulfate) and concentrated, and the residue was distilled to give the title compound (2.0 g); bp 100°–105° C./0.1 torr.

Microanalysis for $C_8H_3NO_3SF_4Cl_2$

Calc'd: S 9.89; Cl 21.55; Found: S 9.48; Cl 19.77.

5. 5,6,7,8-Tetrafluoro-3-methyl-2H-1,2,4-benzothiadiazine, 1,1-dioxide

2-[(1-Chloroethylidine)amino]-3,4,5,6-tetrafluorobenzene sulfonyl chloride (400 mg) was added to concentrated ammonium hydroxide solution (20 mL). A white precipitate formed immediately. The mixture was heated on a steam bath for 30 minutes, resulting in a clear solution. The mixture was cooled to 25° C., filtered, and acidified by addition of 10% hydrochloric acid. A white crystalline solid formed; it was collected, washed with hot water, and dried in vacuo to give the title compound (220 mg); m.p. 290–291° C.

Microanalysis $C_8H_4N_2O_2SF_4$

Calc'd: S 11.95; N 10.45; Found: S 11.85; N 10.68.

B. 4'-[(5,6,7,8-Tetrafluoro-3-methyl-4H-1,2,4-benzothiadiazin-4-yl)methyl][1,1'-biphenyl]-2-carboxylic acid, 1,1-dimethylethyl ester, 1,1-dioxide To a solution of the title A compound (268 mg, 1.0 mmol) and 18-crown-6 (50 mg) in 1,4-dioxane (4 mL) were added potassium hexamethyldisilazide (2.0 mL of 0.7 M solution in hexane, 1.4 mmol) then the title B compound of Example 1 (700 mg, 2 mmol). The resulting mixture was heated at reflux under argon for three hours, after which dimethylpropylene urea (1.0 mL) was added to the heterogeneous mixture. Heating at reflux was continued for another 16 hours, after which the mixture was poured into brine and extracted with ethyl acetate (3×). The extract was washed with brine, dried (magnesium sulfate), and concentrated. The residue was purified by flash chromatography on silica gel (65 g), eluting with a gradient from 4:1 to 1:1 hexanes::ethyl acetate. Unreacted title B compound of Example 1 eluted first, followed quickly by the 2-alkyl isomer (40 mg, 7%). Later fractions containing the 4-isomer (TLC)

were combined and concentrated. The residue was triturated with petroleum ether/ether to give the title compound as a white solid (175 mg, 33%); m.p. 177°–179° C.

C. 4'-[(5,6,7,8-Tetrafluoro-3-methyl-4H-1,2,4-benzothiadiazin-4-)methyl][1,1'-biphenyl]-2-carboxylic acid, 1,1-dioxide The title B compound (150 mg, 0.28 mmol) was dissolved in trifluoroacetic acid (20 mL) and stirred at room temperature for two hours. The solution was concentrated in vacuo to an oil, triturated with methanol and isolated by filtration to give the title compound as a white solid (83 mg, 0.17 mmol, 62 %); m.p. 128°–40° C.

Elemental Analysis (%) for 0.2 $H_2O$

Calc'd: C 54.82; H 3.01; N 5.81; S 6.65; F 15.77; Found: C 54.79; H 3.06; N 5.84; S 6.74; F 15.57.

EXAMPLE 6

3-(Propylthio)-4-[[2'-(1H-tetrazol-5-yl)[1,1'-biphenyl]-methyl]-4H-1,2,4-benzothiadiazine, 1,1-dioxide, monopotassium salt

A. 4'-(Bromomethyl)[1,1 '-biphenyl]-2-carbonitrile

1. 4'-Methyl[1,1'-biphenyl]-2-carboxamide

To a solution of 4'methyl-[1,1'biphenyl]-2-carboxylic acid (20.0 g, 94.2 mmol) in dichloromethane (200 mL) at 0° C. was added dimethylformamide (0.5 mL) followed by oxalyl chloride (100 mL of 2.0M solution in dichloromethane, 200 mmol). The rate of addition was adjusted to maintain the internal temperature below 10° C. When the addition was complete, the mixture was allowed to warm to 25° C. and was stirred at that temperature for two hours, after which it was concentrated in vacuo. The semisolid residue was added portionwise to concentrated ammonium hydroxide solution (250 mL) at 0° C., stirred for 15 minutes, and diluted with water (200 mL). The resulting white precipitate was collected, washed with water, and dried in vacuo over phosphorus pentoxide to give the title compound (18.7 g, 90%).

2. 4'-Methyl[1,1'-biphenyl]-2-carbonitrile

A mixture of the title 1 compound (18.7 g, 88.4 mmol) and thionyl chloride (90 mL) was heated at reflux for four hours, after which it was concentrated in vacuo. The resulting brown solid was crystallized from hexanes (500 mL) to give the title compound in two crops (13.5 g, 80%); m.p. 44–47° C.

3. 4'-(Bromomethyl)[1,1'-biphenyl]-2-carbonitrile

A mixture of the title 2 compound (10.0 g, 51.8 mmol), N-bromosuccinimide (10.0 g, 56.2 mmol), and benzoyl peroxide (1.0 g, 4 mmol) in carbon tetrachloride (1 liter) was heated at reflux under argon for five hours, after which a starch-iodide test was negative. The mixture was then cooled to 25° C., filtered, and concentrated. The semisolid residue was triturated with ether (250 mL) to give the title compound as a free flowing white solid; m.p. 121°–122° C. (7.4 g, 52%). The mother liquor was concentrated and the residue (~5 g) was chromatographed on silica gel (300 g), eluting with hexane:ethyl acetate (10:1) to give recovered starting material (570 mg, 5.7%; m.p. 47°–48° C., Rf 0.52 in 5:1 hexane:ethyl acetate), followed by more of title compound (800 mg, 5.6%, $R_f$ 0.43); m.p. 121°–122° C. The combined yield of the title compound was 8.2 g, 58% (61% after correction for recovered starting material). Satisfactory microanalysis was obtained for C,H,N; slight excess of bromine was indicated (calc'd 28.93%, found 29.75%).

B. 4'-[[3-(Propylthio)-4H-1,2,4-benzothiadiazin-4-yl]methyl][1,1'-biphenyl]-2-carbonitrile, 1,1-dioxide and 4'-[[3-(Propylthio)-2H-1,2,4-benzothiadiazin-2-yl]methyl][1,1'-biphenyl]-2-carbonitrile, 1,1-dioxide A mixture of the title B compound of Example 2 (385 mg, 1.5 mmol), the title A compound (544 mg, 2.0 mmol), potassium tert-butoxide (200 mg, 1.8 mmol) and 18-crown-6 (100 mg) in tetrahydrofuran (5 mL) was stirred at 50° C. for 20 hours. Additional title A compound (270 mg) and potassium tert-butoxide (100 mg) were added and the mixture was stirred at 50° C. for 24 more hours, after which it was poured into brine and extracted with dichloromethane. The extract was dried (magnesium sulfate) and concentrated and the residue was purified by flash chromatography on silica gel (65 g), eluting with 4:1 hexane:ethyl acetate. Fractions containing the high $R_f$ and low $R_f$ major products were combined and rechromatographed with 40:1 methylene chloride: ethyl acetate and with 8:1 hexanes:ethyl acetate, respectively, to give the title compound as a high $R_f$ isomer (260 mg, 39%) and a low $R_f$ isomer (200 mg, 30%).

C. 3-(Propylthio)-4-[[2'-(1H-tetrazol-5-yl)-[1,1'-biphenyl]-methyl]-4H-1,2,4-benzothiadiazine, 1,1-dioxide, monopotassium salt A solution of the low $R_f$ isomer of the title B compound (165 mg, 0.37 mmol), tributyltin azide (490 mg, 1.5 mmol), and xylenes (0.4 ml) was stirred at 100° C. for 17 hours. The mixture was then transferred directly to a column of silica gel (Sorbsil C60, 65 g), and was eluted with 20:13:1 ethyl acetate:hexanes:acetic acid. Fractions containing the major UV absorbing product were combined and concentrated. The residue was dissolved in excess 0.1 N potassium carbonate solution and purified by preparative HPLC (Jordi-Gel polystyrene column, 30×500 mm, eluting with one liter of water then 50 mL/min of a linear gradient from water to methanol over 20 minutes). Fractions having UV absorbance at 300 nm were analyzed by analytical HPLC and those containing the major product were combined and concentrated; the residue was dissolved in ethanol, diluted with water until cloudy, frozen, and lyophilized to give the title compound as a white solid (75 mg, 39%); m.p. 155°–185° C.

Elemental Analysis (%)

Calc'd: C 53.17; H 4.18; N 15.50; S 11.83; Found: C 53.62; H 4.31; N 15.02; S 11.35.

EXAMPLE 7

3-(Propylthio)-2-[[2'-(1H-tetrazol-5-yl)1,1'-biphenyl]4-yl]methyl]-2H-1,2,4-benzothiadiazine, 1,1-dioxide, potassium salt A solution of the high $R_f$ isomer of the title B compound of Example 6 (260 mg, 0.58 mmol), tributyltin azide (770 mg, 2.3 mmol), and xylenes (0.6 mL) was stirred at 90° C. for 17 hours, then at 110° C. for 24 hours. The mixture was then transferred directly to a column of silica gel (Sorbsil C60, 65 g), and was eluted with 18:18:1 ethyl acetate:hexanes:acetic acid. Fractions containing the major UV absorbing product were combined and concentrated. The residue was rechromatographed on silica gel (E. Merck, 65 g), eluting with 10:1 ethyl acetate: (pyridine 20, acetic acid 6, water 11); fractions containing the major UV absorbing product were combined and concentrated. The residue was dissolved in excess 0.1 N potassium carbonate solution and purified by preparative HPLC (Jordi-Gel polystyrene column, 30×500 mm, eluting with one liter of water then 50 mL/min of a linear gradient from water to methanol over 20 minutes). Fractions having UV absorbance at 254 nm were analyzed by analytical HPLC and those containing the major product were combined and concentrated; the residue was dissolved in ethanol, diluted with water until cloudy, frozen, and lyophilized to give the title compound as a white solid (125 mg, 41%); m.p. 95°–115° C.

Elemental Analysis (%)

Calc'd: C 55.16; H 4.57; N 15.23; S 11.62; Found: C 55.05; H 4.49; N 15.63; S 11.23.

EXAMPLE 8

4'-[[7-Methyl-3-(propylthio)-4H-pyrido[2,3-e]-1,2,4-thiadiazin-4-yl]methyl][1,1'-biphenyl]-2-carboxylic acid, 1,1-dioxide A. 2-Amino-5-methyl-3-pyridinesulfonyl chloride Solid 2-amino-5-picoline (10.8 g, 0.10 mol) was added portionwise to chlorosulfonic acid (66 mL, 1.0 mol) at ambient temperature over 5 minutes. When the addition was complete, the mixture was warmed to 140° C. and stirred at that temperature for 2 hours. During the heating period gas evolution was initially rapid and ceased completely after 2 hours. The mixture was then cooled to room temperature and poured onto 2 liters of ice. Solid sodium bicarbonate was added to the resulting solution to adjust the pH to about 7.0. The solid product that precipitated was collected and rinsed with a small amount of cold ethanol. The solid was then dissolved in one liter of hot chloroform, the resulting solution was dried (magnesium sulfate), and the solution was concentrated to a volume of about 100 mL. The solid product that formed was collected, the mother liquor was concentrated to 20 mL and a second crop was collected. The solid products were combined to give the title compound (14.4 g, 70 %); m.p. 16°–166° C.

B. 2-Amino-5-methyl-3-pyridinesulfonamide

A mixture of the title A compound (10.0 g, 48.5 mmol) and concentrated ammonium hydroxide solution (150 mL) was stirred at 25° C. for 16 hours, after which it was concentrated in vacuo to one-half its original volume. The residue was diluted with saturated sodium bicarbonate solution and extracted with ethyl acetate (3×) The extract was dried and concentrated, and the residue was triturated with ether to give a yellow solid, m.p. 187–189° C. The solid was recrystallized from absolute ethanol (200 mL) to give the title compound as a white solid (6.5 g, 72%); m.p. 191°–192° C.

C. 4'-[[3-(Aminosulfonyl)-5-methyl-2-pyridinyl]-amino]-methyl][1,1'-biphenyl]-2-carboxylic acid, 1,1-dimethylethyl ester Trimethylsilyl chloride (1.4 mL, 11.0 mmol) was added to a solution of the title B compound (1.00 g, 5.35 mmol) in tetrahydrofuran (20 mL) under argon. The mixture was stirred at 25° C. for 15 minutes, resulting in a dense white precipitate. Sodium hydride (1.0 g of 60% dispersion in oil, 25 mmol) was then added, and the mixture was heated at reflux for 5 minutes until gas evolution ceased. The title B compound of Example 1 (2.1 g, 6 mmol) was then added and the mixture was heated at reflux for 6 hours. Additional sodium hydride (1.0 g, 25 mmol) was added, and reflux was continued for a total of 18 hours. The mixture was then poured into brine, extracted with ethyl acetate (2×), dried, and concentrated. The residue was purified by flash chromatography on silica gel (EM, 300 g), eluting with 1:1 hexane:ethyl acetate, to give the title compound as the major product (650 mg, 27%).

4-[[7-Methyl-3-(propylthio)-4H-pyrido-[2,3-e]-1,2,4-thiadiazin-4-yl]methyl][1,1'-biphenyl]-2-carboxylic acid, 1,1-dimethyl-ethyl ester, 1,1-dioxide A mixture of the title C compound (120 mg, 0.26 mmol), thiocarbonyldiimidazole (92 mg, 0.52 mmol), 1,8-diazabicyclo[5.4.0]undec-7-ene (0.116 mL, 0.78 mmol), and dimethylaminopyridine (5 mg, 0.04 mmol) in tetrahydrofuran (2.6 mL) was stirred under argon for 18 hours. The mixture was then poured into brine, extracted with ethyl acetate, washed with pH 4.0 buffer solution, dried, and concentrated in vacuo. The residue was dissolved in dimethylformamide (2 mL). Cesium carbonate (169 mg, 0.5 mmol) and n-propyl iodide (0.1 mL, 1 mmol) were added and the mixture was stirred at 25° C. for 4 hours. The mixture was then poured into brine, extracted with ethyl acetate, dried, and concentrated. The residue was purified by flash chromatography on silica gel (60 g), eluting with 3:1 hexane:ethyl acetate, to give an intermediate (115 mg, 82%). The sample was further purified by trituration with petroleum ether containing a trace of ether, to give the title compound as a white solid, m.p. 146°–148° C.

E. 4'-[[7-Methyl-3-(propylthio)-4H-pyrido[2,3-e]-1,2,4-thiadiazin-4-yl]methyl][1,1'-biphenyl]-2-carboxylic acid, 1,1-dioxide A solution of the title D compound (115 mg, 0.21 mmol) in trifluoroacetic acid (5 mL) was stirred at 25° C. for 2 hours, after which it was concentrated in vacuo. The residue was purified by preparative HPLC (YMC S-10 ODS column, 30×500 mm, eluting with 50 mL/min of 74% aqueous methanol containing 0.1% trifluoroacetic acid). Fractions containing the major product (retention time, 11 minutes) were combined and concentrated in vacuo. The residue was triturated with methanol to give the title compound (75 mg, 73%); m.p. 237°–239° C.

Elemental Analysis (%)

Calc'd: C 59.86; H 4.81; N 8.73; S 13.31; Found: C 59.86; H 4.66; N 8.70; S 13.09.

EXAMPLE 9

7-Methyl-3-(propylthio)-4-[2'-(1H-tetrazol-5-yl)-[1,1'-biphenyl]-4-ylmethyl]-4H-pyrido[2,3-e]1,2,4-thiadiazine, 1,1-dioxide

A.
4'-[[3-(Aminosulfonyl)-5-methyl-2-pyridinyl]-amino]-methyl][1,1'-biphenyl]-2-carbonitrile Trimethylsilyl chloride (1.4 mL, 11.0 mmol) was added to a solution of the title B compound of Example 8 (1.00 g, 5.35 mmol) in tetrahydrofuran (20 mL) under argon. The mixture was stirred at 25° C. for 15 minutes, resulting in a dense white precipitate. Sodium hydride (1.0 g of 60% dispersion in oil, 25 mmol) was then added, and the mixture was heated at reflux for 15 minutes until gas evolution ceased. The title A compound of Example 6 (2.1 g, 6 mmol) was then added and the mixture was heated at reflux for 6 hours. Additional sodium hydride (1.0 g, 25 mmol) was added, and reflux was continued for a total of 18 hours. The mixture was then poured into brine, extracted with ethyl acetate (2×), dried, and concentrated. The residue was purified by flash chromatography on silica gel (EM, 300 g), eluting with 1:1 hexane:ethyl acetate, to give the title compound as the major product (210 mg, 10%).

B.
4'-[[7-Methyl-3-(propylthio)-4H-pyrido-[2,3-e]-1,2,4-thiadiazin-4-yl]methyl][1,1'-biphenyl]-2-carbonitrile, 1,1-dioxide A mixture of the title A compound (140 mg, 0.37 mmol), thiocarbonyldiimidazole (132 mg, 0.74 mmol), 1,8-diazabicyclo[5.4.0]undec-7-ene (0.162 mL, 1.1 mmol), and dimethylaminopyridine (8 mg, 0.06 mmol) in tetrahydrofuran (3.7 mL) was stirred under argon for 18 hours. The mixture was then poured into brine, extracted with ethyl acetate, washed with pH 4.0 buffer solution, dried, and concentrated in vacuo. The residue was dissolved in dimethylformamide (3 mL). Cesium carbonate (325 mg, 1.0 mmol) and n-propyl iodide (0.2 mL, 2 mmol) were added and the mixture was stirred at 25° C. for 4 hours. The mixture was then poured into brine, extracted with ethyl acetate, dried, and concentrated. The residue was purified by flash chromatography on silica gel (60 g), eluting with 3:1 hexane:ethyl acetate. The product was further purified by trituration with methanol to give the title compound as a white solid (118 mg, 69%); m.p. 190–192° C.

C.
7-Methyl-3-(propylthio)-4-[2'-(1H-tetrazol-5-yl)[1,1'-biphenyl]-4-ylmethyl]-4H-pyrido-[2,3-e]1,2,4-thiadiazine, 1,1-dioxide A mixture of the title B compound (130 mg, 0.28 mmol), o-xylene (0.3 mL), and tributyltin azide (465 mg, 1.4 mmol) was stirred at 115° C. for 20 hours, after which the mixture was transferred directly to a silica gel column. The column was eluted with 10:10:1 hexane:ethyl acetate:acetic acid. Fractions containing the major UV active product ($R_f$=0.5) were combined, diluted with an equal volume of toluene, and concentrated. The residue was purified by preparative HPLC (YMC S-10 ODS column, 30×500 mm, eluting with 50 mL/minute of 74% aqueous methanol containing 0.1% trifluoroacetic acid). Fractions containing the major product (retention time, 14 minutes) were combined and concentrated in vacuo. The residue was triturated with methanol to give the title compound (85 mg, 60%); m.p. 158–160° C.

Elemental Analysis (%)

Calc'd: C 57.01; H 4.58; N 19.39; S 12.68; Found: C 56.93; H 4.39; N 19.15; S 12.31.

EXAMPLE 10

3-(Propylthio)-4-[[2'-(2H-tetrazol-5-yl)[1,1'-biphenyl]-4-yl]methyl]-4H-1,2,4-benzothiadiazine-6-carboxylic acid, 1,1-dioxide

A. 4-Fluoro-3-nitrobenzenecarboxylic acid, methyl ester

Potassium carbonate (149 g, 1.08 mol) and iodomethane (252 mL, 4.05 mol) were added to a solution of 4-fluoro-3-nitrobenzoic acid (50 g, 0.27 mol) in dry acetone (700 mL) under argon. Overhead mechanical stirring was carried out for 16 hours. The reaction mixture was filtered, and acetone was removed under vacuum. The residue was partitioned between ethyl acetate and saturated potassium carbonate solution, the aqueous layer was washed with ethyl acetate, the combined organic layers were washed with saturated potassium carbonate solution, brine, dried over sodium sulfate, and concentrated to yield the title compound as a light yellow solid; m.p. 58.5°–59.50° C.

Analysis for $C_8H_6FNO_4$

Calc'd: C 48.25; H 3.04; N 7.03; F 9.54; Found: C 48.23; H 2.86; N 6.86; F 9.13.

B. 3-Nitro-4-sulfobenzenecarboxylic acid, methyl ester, monosodium salt

A suspension of the title A compound (38 g, 0.19 mol) and $Na_2SO_3$ (19 g, 0.15 mol) in 50% aqueous ethanol (510 mL) was refluxed for 30 minutes. After cooling to room temperature, the reaction mixture was concentrated to near dryness. The residue was suspended in refluxing methanol (500 mL) and filtered. The filtrate was evaporated and the residue was triturated with 98:2 ether:ethyl acetate (250 mL) to yield the title compound (33 g, 78%) as a light yellow solid; m.p.>300° C.

C. 4-(Chlorosulfonyl)-3-nitrobenzenecarboxylic acid, methyl ester

Thionyl chloride (128 mL, 1.76 mmol), was added to the title B compound (37 g, 0.13 mol) at room temperature. The addition of dimethylformamide (0.1 mL) to the stirred solution initiated gas evolution. The mixture was heated at reflux for four hours. Reaction progress was monitored by HPLC (0% to 100% B, 30 minute gradient), which after two hours reflux time indicated the presence of <5% unconsumed sulfonate salt. After cooling to room temperature, thionye chloride was evaporated. Trituration of the solid residue with hexanes (400 mL) yielded the title compound as a light yellow solid; m.p. 96.0°–98.5° C. with foaming.

D. 4-(Aminosulfonyl)-3-nitrobenzenecarboxylic acid, methyl ester

To a suspension of the title C compound (30 g, 0.11 mol) in t-butyl alcohol (600 mL) was added saturated ammonia/t-butyl alcohol solution (360 mL). The reaction mixture was stirred for 1.5 hours and concentrated under vacuum to yield a yellow solid which was dissolved in ethyl acetate and washed with saturated aqueous potassium bicarbonate solution. The aqueous layer was extracted with ethyl acetate, the combined ethyl acetate layers were washed with saturated aqueous potassium bicarbonate solution (2×), water, brine, dried over sodium sulfate, and evaporated to yield a yellow, somewhat oily solid. Flash chromatography on silica gel (75 g), eluting with 98:2 methylene chloride:methanol, 96:2:2 methylene chloride:methanol:acetic acid, and 96:2:2 ethyl acetate:methanol:acetic acid yielded the title compound (19 g, 67%) as a light yellow solid; m.p. 138–141° C.

Analysis for $C_8H_8N_2O_6S$

Calc'd: C 36.93; H 3.10; N 10.77; S 12.32; Found: C 37.10; H 2.93; N 10.82; S 12.14.

4-(Aminosulfonyl)-3-nitrobenzenecarboxylic acid

Potassium hydroxide (148 mL, 2M solution, 0.296 mol) was slowly added to a stirred solution of the title D compound (19.3 g, 0.074 mol) in methanol (270 mL). After 50 minutes, the reaction mixture was acidified to pH 1.0 with concentrated hydrochloric acid. Methanol was evaporated and the resulting aqueous suspension was diluted with ethyl acetate and water. The aqueous layer was washed with ethyl acetate, the combined organic layers were washed with water (2×), brine, dried over sodium sulfate and concentrated to yield an off-white solid. Trituration with 90:10 water:methanol (1.0L) followed by drying under vacuum over $P_2O_5$ yielded the title compound (15.3 g, 84%) as a white solid; m.p. 272°–275.5° C. dec.

Analysis for $C_7H_6N_2O_6S$

Calc'd: C 34.15; H 2.46; N 11.38; S 13.02; Found: C 34.30; H 2.41; N 11.56; S 12.62.

F. 4-(Aminosulfonyl)-3-nitrobenzenecarboxylic acid, 4-methoxyphenyl)methyl ester To a stirred solution of the title E compound (12.5 g, 50.7 mmol) in dimethylformamide (125 mL, room temperature, argon) was added 4-methoxybenzyl alcohol (6.96 mL, 55.8 mmol), 4-dimethylamino pyridine (0.62 g, 5.1 mmol), and dicyclohexylcarbodiimide (11.51 g, 55.8 mmol). After 4.25 hours, dimethylformamide was removed under vacuum. The residue was diluted with ethyl acetate and washed twice with potassium bisulfate solution (0.25M), saturated potassium bicarbonate solution (3×), brine, dried over sodium sulfate, and evaporated to yield a yellow semisolid (18.6 g). Flash chromatography on silica gel (750 g,), eluting with 95:5 and 85:15 hexanes:ethyl acetate yielded the title compound (7.76 g, 42%) as a yellow crystalline solid; m.p. 128.5°–130.5° C.

Analysis for $C_{15}H_{24}N_2O_7S$

Calc'd: C 49.18; H 3.85; N 7.65; S 8.75; Found: C 49.49; H 3.73; N 7.56; S 8.96.

G. 3-Amino-4-(aminosulfonyl)benzenecarboxylic acid, (4-methoxyphenyl)methyl ester A solution of the title F compound (7.74 g, 23.0 mmol) in ethyl acetate (250 mL) with Raney Nickel (0.77 g) was hydrogenated at 1 atm for 5.5 hours. Reaction progress was followed by HPLC (62% B, isocratic), in which initial formation of a reaction intermediate and its subsequent transformation to the desired product were observed. The reaction mixture was filtered through Celite and evaporate to yield the title compound (6.78 g, 88%) as a white solid.

Recrystallization of the title compound (50 mg) from 95% ethanol (1 crop) yielded analytically pure material (29 mg); m.p. 148.5–150° C.

Analysis for $C_{15}H_{16}N_2O_5S$

Calc'd: C 53.56; H 4.79; N 8.33; S 9.53; Found: C 53.87; H 4.68; N 8.18; S 9.21.

H. 3-Mercapto-4H-1,2,4-benzothiadiazine-6-carboxylic acid, 1,1-dioxide, (4-methoxyphenyl) methyl ester A solution of the title G compound (1.0 g, 3.0 mmol) and 1,1'-thiocarbonyldiimidazole (0.64 g, 3.57 mmol) in anhydrous, degassed dimethylformamide (6 mL) was treated with cesium carbonate (2.2 g, 6.64 mmol). The reaction mixture was stirred for two hours. An additional portion of 1,1'-thiocarbonyldiimidazole (0.10 g, 0.56 mmol) followed by 2.3 hours reaction time were required to completely consume the substrate, based on reaction progress assessment by HPLC (62% B, isocratic). The reaction mixture was adjusted to pH 3.0 with 0.25M potassium bisulfate solution. The crude product was extracted with ethyl acetate (3×), the combined ethyl acetate layers were washed with 1:1 brine:0.25M potassium bisulfate solution, brine, dried over sodium sulfate and evaporated to yield a light tan hard taffy (1.03 g). Flash chromatography on silica gel (62 g), eluting with 1:1 hexanes:ethyl acetate, 3:2 ethyl acetate:hexanes, 4:1 ethyl acetate:hexanes, and 99:1 ethyl acetate:methanol yielded an off-white, somewhat sticky solid (0.83 g). The solid was suspended in ether, collected by filtration, and rinsed with ether to yield the title compound (0.65 g, 58%) as an off-white powder; m.p. 249°–252° C. foam/dec.

I.
3-(propylthio)-4H-1,2,4-benzothiadiazine-6-carboxylic acid, 1,1-dioxide, (4-methoxyphenyl) methyl ester To a stirred solution of the title H compound (0.56 g, 1.5 mmol) in anhydrous dimethylformamide (3.6 mL) was added 1-iodopropane (0.40 mL, 4.1 mmol). After 30 minutes, 0.25M potassium bisulfate solution (32 mL) were added, the crude product was extracted sequentially with chloroform and ethyl acetate. The separately combined organic layers were each washed with 0.25M potassium bisulfate solution, recombined, dried over sodium sulfate and evaporated to yield the title compound as a tan solid. Trituration with 75:25 hexanes:ethyl acetate (100 mL) yielded a light tan solid (0.49 g, 79%); m.p. 185.5°–187° C. with foaming.

Analysis for $C_{19}H_{20}N_2O_5S_2$

Calc'd: C 53.52; H 4.88; N 6.57; S 15.04; Found: C 53.58; H 4.68; N 6.71; S 14.78.

J.
4-[(2'-Cyano[1,1'-biphenyl]-4-yl)methyl]-3-(propylthio)-4H-1,2,4-benzothiadiazine-6-carboxylic acid, 1,1-dioxide, (4-methoxyphenyl) methyl ester and 2-[(2'-Cyano [1,1'-biphenyl]-4-yl)methyl]-3-(propylthio)-2H-1,2,4-benzothiadiazine-6-carboxylic acid, 1,1-dioxide, (4-methoxyphenyl) methyl ester A solution of the title I compound (0.49 g, 1.7 mmol), potassium t-butoxide (0.16 g, 1.39 mmol), and 18-Crown-6 (0.77 mg, $3.0 \times 10^{-3}$ mmol) in tetrahydrofuran (4.0 mL) was stirred for 20 minutes. The title A compound of Example 6 was added (0.42 g, 1.5 mmol) and the reaction mixture was heated at reflux for 16 hours.

HPLC analysis (0% to 100%B, 30 minute gradient) indicated the presence of unconsumed title I compound. An additional portion of the title A compound of Example 6 was added (0.16 g, 0.59 mmol) and reflux was continued for three hours, 20 minutes. HPLC analysis after two hours reflux time indicated the presence of a small trace of unconsumed title I compound (3.3%). Tetrahydrofuran was evaporated. The residue was flash-chromatographed on silica gel (43 g), eluting with methylene chloride, 99:1 methylene chloride:ethyl acetate, and 95:5 methylene chloride:ethyl acetate to yield 2-[(2′-Cyano[1,1′-biphenyl]-4-yl)methyl]-3-(propylthio)-2H-1,2,4-benzothiadiazine-6-carboxylic acid, 1,1-dioxide, (4-methoxyphenyl)methyl ester (0.24 g, 34%) as a white solid, ($R_f$ 0.67 in 95:5 methylene chloride: ethyl acetate); m.p. 53°–68° C.

Fractions containing a more polar ($R_f$ 0.45) were combined and concentrated to an oily white glass (0.15 g). Flash chromatography on silica gel (14 g), eluting with methylene chloride, 99:1 methylene chloride:ethyl acetate and 95:5 methylene chloride:ethyl acetate yielded an off-white solid (100 mg). Recrystallization from 95% ethanol (3 crops, collected at 0° C.) yielded 4-[(2′-Cyano[1,1′-biphenyl]-4-yl)methyl]-3(propylthio)-4H-1,2,4-benzothiadiazine-6-carboxylic acid, 1,1-dioxide, (4-methoxyphenyl)methyl ester as a white solid (73 mg, 11%).

K. 3-(Propylthio)-4-[[2′-(2H-tetrazol-5-yl)[1,1′-biphenyl]-4-yl]methyl]-4H-1,2,4-benzothiadiazine-6-carboxylic acid, 1,1-dioxide A slightly cloudy solution of 4-[(2′Cyano [1,1′-biphenyl]-4-yl)methyl]-3-(propylthio)-4H-1,2,4-benzothiadiazine-6-carboxylic acid, 1,1-dioxide, (4-methoxyphenyl)methyl ester (75 mg, 0.12 mmol), tri-n-butyltin azide (179 mg, 0.54 mmol), and o-xylene (0.13 mL) was heated to 85° C. for 16 hours, 100° C. for six hours, and 115° C. for 16 hours. TLC analysis of the reaction mixture revealed the presence of unreacted 4-[(2′-Cyano[1,1′-biphenyl]-4-yl)methyl]3-(propylthio)-4H-1,2,4-benzothiadiazine-6-carboxylic acid, 1,1-dioxide, (4-methoxyphenyl)-methyl ester. An additional portion of tri-n-butyltin azide (44 mg, 0.12 mmol) and o-xylene (0.13 mL) was introduced to the solidified reaction mixture, and stirring of the viscous, homogenous reaction solution at 130° C. was continued for 6.25 hours. After cooling to room temperature, the reaction mixture was adsorbed on Celite and flash-chromatographed on Sorbisil C 60 silica gel (16 g), eluting with 14:10:1 ethyl acetate: hexanes:acetic acid and 14:10:1 hexanes::ethyl acetate:acetic acid to yield a white solid (59 mg, 91%).

Analysis for $C_{25}H_{22}N_6O_4S_2 \cdot 0.10 C_2HF_3O_2$

Calc'd: C 55.44; H 4.08; N 15.20; Found: C 55.44; H 3.70; N 15.20.

EXAMPLE 11

3-(Ethylthio)-7-methyl-4-[[2′-(1H-tetrazol-5-yl-[1,1′-biphenyl]-4-yl]methyl]-4H-pyrido[2,3-e]1,2,4-thiadiazine, 1,1-dioxide The above titled compound was prepared using the procedure described in Example 8, except that in part D, ethyl iodide was employed instead of n-propyl iodide. The title compound had a melting point of 213° C. to 216° C.

Analysis for $C_{23}H_{21}N_7O_4S_2 \cdot 0.25 H_2O$

Calc'd: C 55.69; H 4.37; N 19.76; S 12.93; Found: C 55.88; H 4.18; N 19.76; S 12.55.

What is claimed is:

1. A compound of the formula

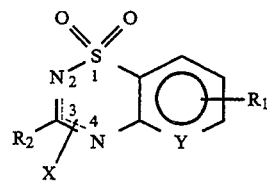

or a pharmaceutically acceptable salt thereof;

wherein the broken lines between the nitrogen atoms represent the presence of double bonds, and either the 2,3-position is bonded by a double bond and the 4-position nitrogen atom bears the group X, or the 3,4-position is bonded by a double bond and the 2-position nitrogen atom bears the group X, where the group X is

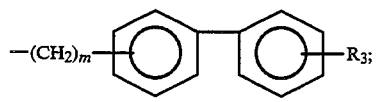

Y is a carbon or nitrogen atom;

$R_1$ is hydrogen, —$CO_2R_4$, —$COR_4$, perfluoroalkyl, halogen, cyano or

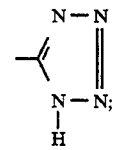

$R_2$ is hydrogen, alkyl, alkenyl, alkynyl, arylalkyl, —$OR_7$ or —$SR_7$ bonded to the ring system by a single bond or $R_2$ is O or S bonded to the ring system by a double bond to form a carbonyl or thiocarbonyl group;

$R_3$ is

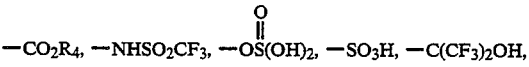

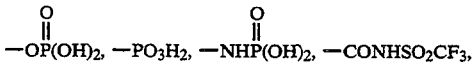

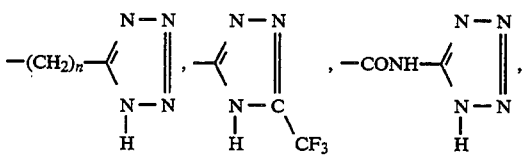

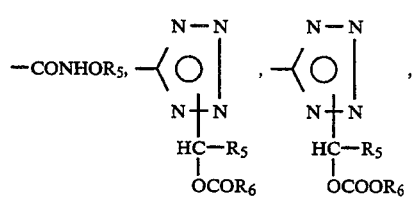

-continued

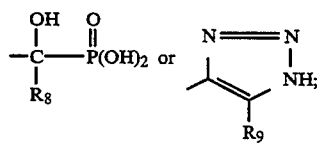

$R_4$ is hydrogen, alkyl, perfluoroalkyl of 1 to 8 carbon atoms, cycloalkyl of 3 to 6 carbon atoms, phenyl, benzyl,

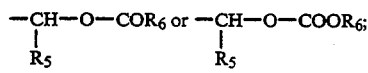

$R_5$ is hydrogen, alkyl, aryl, arylalkyl or cycloalkyl;
$R_6$ is alkyl, aryl, alkylaryl, arylalkyl or cycloalkyl;
$R_7$ is hydrogen, alkyl, alkenyl, alkynyl, aryl or arylalkyl;
$R_8$ is hydrogen, alkyl of 1 to 5 carbon atoms or phenyl;
$R_9$ is —CN, —NO$_2$ or -CO$_2$R$_4$;
m is an integer of 1 to 5;
n is 0 or the integer 1;
wherein "alkyl" refers to both straight and branched chain hydrocarbons, containing 1 to 12 carbon atoms in the normal chain and the various branched chain isomers thereof, optionally substituted with halo, alkoxy, aryl, alkylaryl, haloaryl, cycloalkyl, alkylcycloalkyl, hydroxy, alkylamine, alkanoylamino, nitro, cyano, thiol or alkylthio;
"alkenyl" refers to said "alkyl" groups further having at least one carbon to carbon double bond;
"alkynyl" refers to said "alkyl" groups further having at least one carbon to carbon triple bond; and
"aryl" refers to phenyl and phenyl substituted with 1, 2 or 3 amino, halogen, hydroxy, trifluoromethyl, alkyl (of 1 to 4 carbon atoms), alkoxy (of 1 to 4 carbon atoms), alkanoyloxy, aminocarbonyl, or carboxy groups.

2. A compound of claim 1 wherein $R_1$ is —CO$_2$H.
3. A compound of claim 1 wherein $R_2$ is —OR$_7$ or —SR$_7$, where $R_7$ is alkyl.
4. A compound of claim 1 wherein $R_3$ is —CO$_2$H or tetrazolyl and is bonded at the 2-position.
5. A compound of claim 1 wherein Y is a carbon atom.
6. A compound of claim 1 wherein m is the integer 1.
7. A compound of claim 1 wherein
$R_1$ is —CO$_2$H;
$R_2$ is —OR$_7$ or —SR$_7$, where $R_7$ is alkyl;
$R_3$ is —CO$_2$H or tetrazolyl and is bonded at the 2-position;
Y is carbon; and
m is the integer 1.
8. A compound of claim 1, 4'-[(3-Butyl-2H-1,2,4-benzothiadiazin-2-yl)methyl][1,1'-biphenyl]-2-carboxylic acid, 1,1-dioxide or a pharmaceutically acceptable salt thereof.
9. A compound of claim 1, 4'-[[3-(Propylthio)-2H-1,2,4-benzothiadiazin-2-yl]methyl]-[1,1'-biphenyl]-2-carboxylic acid, 1,1-dioxide or a pharmaceutically acceptable salt thereof.
10. A compound of claim 1, 4'-[(3-Butyl-4H-1,2,4-benzothiadiazin-4-yl)methyl][1,1'-biphenyl]-2-carboxylic acid, 1,1-dioxide or a pharmaceutically acceptable salt thereof.
11. A compound of claim 1, 4'-[[3-(Propylthio)-4H-1,2,4-benzothiadiazin-4-yl]methyl]-[1,1'-biphenyl]-2-carboxylic acid, 1,1-dioxide or a pharmaceutically acceptable salt thereof.
12. A compound of claim 1, 4'-[(5,6,7,8-Tetrafluoro-3-methyl-4H-1,2,4-benzothiadiazin-4-yl)methyl][1,1'-biphenyl]-2-carboxylic acid, 1,1-dioxide or a pharmaceutically acceptable salt thereof.
13. A compound of claim 1, 3-(Propylthio)-2-[[2'-(1H-tetrazol-5-yl)1,1'-biphenyl]-4-yl]methyl]-2H-1,2,4-benzothiadiazine, 1,1-dioxide or a pharmaceutically acceptable salt thereof.
14. A compound of claim 1, 4'-[[7-Methyl-3-(propylthio)-4H-pyrido[2,3-e]-1,2,4-thiadiazin-4-yl]methyl][1,1'-biphenyl]-2-carboxylic acid, 1,1-dioxide or a pharmaceutically acceptable salt thereof.
15. A compound of claim 1, 7-Methyl-3-(propylthio)-4-[2'-(1H-tetrazol-5-yl)[1,1'-biphenyl]-4-ylmethyl]-4H-pyrido[2,3-e]1,2,4-thiadiazine, 1,1-dioxide or a pharmaceutically acceptable salt thereof.
16. A compound of claim 1, 3-(Propylthio)-4-[[2'-(2H-tetrazol-5-yl)[1,1'-biphenyl]-4-yl]methyl]-4H-1,2,4-benzothiadiazine-6-carboxylic acid, 1,1-dioxide or a pharmaceutically acceptable salt thereof.
17. A compound of claim 1, 3-(Ethylthio)-7-methyl-4-[[2'-(1H-tetrazol-5-yl)[1,1'-biphenyl]-4-yl]methyl]-4H-pyrido[2,3-e]1,2,4-thiadiazine, 1,1-dioxide or a pharmaceutically acceptable salt thereof.
18. A compound of claim 1, 3-(Propylthio)-4-[[2'-(1H-tetrazol-5-yl)[1,1'-biphenyl]methyl]-4H-1,2,4-benzothiadiazine, 1,1-dioxide or a pharmaceutically acceptable salt thereof.
19. A pharmaceutical composition comprising a compound of claim 1 and a pharmaceutically acceptable carrier.

* * * * *